United States Patent [19]

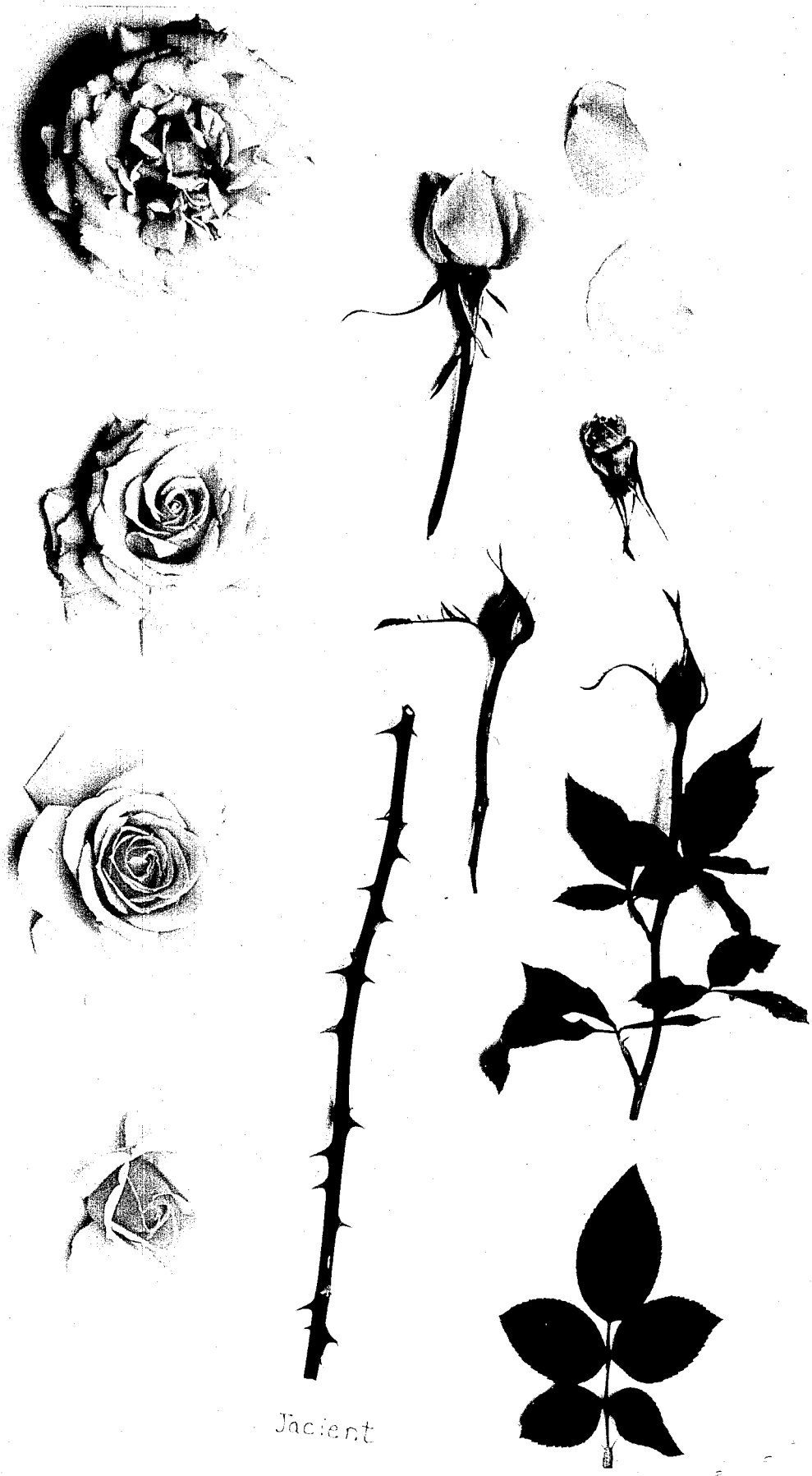
Jacient

Warriner

[11] Patent Number: Plant 6,725

[45] Date of Patent: Apr. 11, 1989

[54] ROSE PLANT JACIENT

[75] Inventor: William A. Warriner, Tustin, Calif.

[73] Assignee: Jackson & Perkins Company, Medford, Oreg.

[21] Appl. No.: 121,748

[22] Filed: Nov. 17, 1987

[51] Int. Cl.[4] ..... A01H 5/00

[52] U.S. Cl. ..... Plt./18

[58] Field of Search ..... Plt. 18

*Primary Examiner*—James R. Feyrer

*Attorney, Agent, or Firm*—Majestic, Parsons, Siebert & Hsue

[57] ABSTRACT

A rose variety of the grandiflora class is provided having glossy mature foliage resistant to mildew and blackspot on a vigorous upright plant reaching five feet bearing flowers in the coral pink range.

1 Drawing Sheet

SUMMARY OF THE INVENTION

The present invention relates to a new and distinct variety of rose plant of the grandiflora class, which was originated by me by crossing the variety Impatient with an unnamed variety.

The primary objective of this breeding was to produce a new rose variety of the grandiflora class having glossy foliage of good disease resistance and a vigorous plant bearing many flowers in the coral pink range. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. An upright habit, reaching five feet in height.
2. Very glossy mature foliage, reddish new foliage.
3. Medium number of prickles on the stems.
4. Flower petals of a light coral pink color on the upper sides and deep coral pink on lower sides.
5. Little or no fragrance.

Asexual reproduction of this new variety by budding, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE INVENTION

The following is a detailed description of my new rose cultivar, which has been denominated "Jacient". Color terminology is in accordance with The Royal Horticultural Society Colour Chart except where an ordinary dictionary significance for the color is apparent.

Observations of the buds and flowers were made from specimens grown in a garden environment at Irvine, Calif. in September.

Flower

The blooming habit is continuous. The bud size is one to one and one-eighth inches when the petals start to unfurl. The bud form is pointed ovoid. The bud color when sepals first divide is near Red Group 52B. When half blown, the upper side of petals is near Red Group 49C with a large Yellow Group 13B area at the base. The lower side of petals is near Red Group 52B with a small Yellow Group 13B area at the base. The sepals have a color near Yellow-Green Group 144A. The surface texture is glabrous. There are three lightly appendaged sepals, and two unappendaged sepals with hairy edge. The receptacle color is near Yellow-Green Group 144A with a funnel shape, broad, small size and smooth, glabrous surface. The peduncle is medium, and has a prickly and glandular surface. Peduncle color is light green and the peduncle is stiff and erect. The petals unfold slowly.

Bloom

Bloom size is medium, with an average open size of three to four inches, borne singly and several together. The stems are strong and medium in length. The form when first open is high center and is retained to the end with the outer petal edges slightly curled. Under normal conditions there are 25 to 30 petals. The upper side of petals at the flower center is near Red Group 49C, and the reverse side of the petals at the flower center is near Red Group 52B. The base of petals is near Yellow Group 13B. The major color on the upper side is near Red Group 49C and on the lower side is near Red Group 52B. There are no variegations. The general tonality at the end of the first day shows no change in color. At the end of the third day, there is still no change in color.

The fragrance is slight. The petal texture is thick, of a round shape, and the tips are slightly recurved.

The arrangement is imbricated with few pentaloids in the center. The blooms drop off cleanly, and last on the plant for a long period and as a cut flower for a long time.

Reproductive Parts

The anthers are medium, of yellow color, arranged regularly around the styles. The filaments are yellow, the pollen is gold yellow, the styles are red, and the stigmas are pale yellow.

Plant

A very vigorous, upright growth of bush form.

Foliage

Medium size, abundant in quantity. The new foliage is reddish colored. The old foliage is near Green Group 139A. Normal mid-stem leaves have five leaflets.

The leaflets have an oval pointed shape, are glossy and smooth, and have a serrated edge. The serration is single and small. Petiole rachis is green, and petiole underside has prickles. Stipules are medium and bearded. The foliage is resistant to mildew and black-spot under normal growing conditions at Irvine, Calif.

Wood

New wood is light green with a smooth bark. Old wood is green with a smooth bark.

Prickles

There are an ordinary number of prickles on main canes from the base and few on laterals from the main canes. The form is long and hooked downward. There are no small prickles on the main stalks or laterals, as small prickles occur only on peduncles.

Parentage

The seed parent was of the variety Impatient. The pollen parent was an unnamed variety.

Classification

Botanical is rosa hybrid. Commercial is grandiflora.

I claim:

1. A new and distinct variety of rose plant and parts thereof of the grandiflora class substantially as herein shown and described, characterized particularly as to novelty by the unique combination of a vigorous, upright habit, a medium number of prickles, glossy mature foliage and coral pink flowers.

* * * * *